United States Patent [19]

Jonas et al.

[11] Patent Number: 4,474,708
[45] Date of Patent: Oct. 2, 1984

[54] PROCESS FOR THE PRODUCTION OF 1,4-BIS-(DICYANO-METHYLENE)-CYCLOHEXANE

[75] Inventors: Friedrich Jonas, Aachen; Jürgen Hocker, Bergisch-Gladbach, both of Fed. Rep. of Germany

[73] Assignee: Bayer Aktiengesellschaft, Leverkusen, Fed. Rep. of Germany

[21] Appl. No.: 456,965

[22] Filed: Jan. 10, 1983

[30] Foreign Application Priority Data

Jan. 20, 1982 [DE] Fed. Rep. of Germany ....... 3201484

[51] Int. Cl.³ ................... C07C 120/00; C07C 121/48
[52] U.S. Cl. ..................................................... 260/464
[58] Field of Search ........................................ 260/464

[56] References Cited

U.S. PATENT DOCUMENTS 3,097,227  7/1963  Williams ..................... 260/465 H
3,162,641 12/1964  Acker et al. ................ 260/464 X
4,229,364 10/1980  Crawford ...................... 260/464

OTHER PUBLICATIONS

Acker, et al., J.A.C.S., 84, (1962), pp. 3370–3374.
Melby, et al., J.A.C.S., 84, (1962), pp. 3374–3387.

*Primary Examiner*—Joseph Paul Brust
*Attorney, Agent, or Firm*—Connolly and Hutz

[57] ABSTRACT

A process for the production of 1,4-bis-(dicyanomethylene)-cyclohexane from a cyclohexane-1,4-dione-2,5-dicarboxylic acid alkylester by saponification with water, optionally under pressure, and by subsequent or simultaneous condensation with malonic acid dinitrile, optionally with the assistance of a catalyst.

2 Claims, No Drawings

PROCESS FOR THE PRODUCTION OF 1,4-BIS-(DICYANO-METHYLENE)-CYCLOHEXANE

This invention relates to a new process for the production of 1,4-bis-(dicyanomethylene)-cyclohexane.

1,4-bis(dicyanomethylene)-cyclohexane is a known and commercially important intermediate in the production of 7,7,8,8-tetracyanoquinodimethane (TCNQ). As an electron acceptor, this compound is capable of forming with electron donors charge-transfer complexes of a high electrical conductivity, and it thus has an increasing commercial significance (see J. AM. Chem. Soc. 84, 3374 (1962)).

This invention provides a novel process for the production of 1,4-bis-(dicyanomethylene)-cyclohexane, wherein a cyclohexane-1,4-dione-2,5-dicarboxylic acid alkyl ester is treated with water under a pressure of from 1 to 200 bars and at a temperature of from 80° to 250° C., and the resulting aqueous solution is reacted with malonic acid dinitrile, optionally in the presence of a catalyst, at a temperature of from 0° to 100° C.

The reaction generally produces a total yield of more than 90% of the theoretical yield.

Starting compounds which are suitable for the present process are cyclohexane-1,4-dione-2,5-dicarboxylic acid alkyl esters corresponding to formula (I):

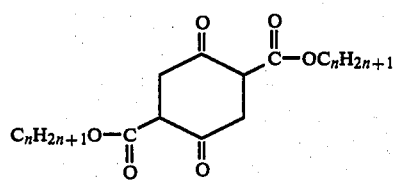

wherein n represents an integer of from 1 to 6.

The above-described reaction with water (saponification and decarboxylation) and the condensation with malonic acid dinitrile can be carried out in one vessel ("one-shot reaction") in water or in a water-containing organic or inorganic solvent.

Suitable solvents wherein the reaction with water can be carried out include alkanols, such as ethanol, butanol; dimethyl-formamide; glycols such as ethylene glycol and dialkyl sulphoxides, and most preferably dimethyl sulphoxide.

The quantity of organic or inorganic solvent may be from 0 to 100, preferably from 0 to 5 parts by weight per part by weight of cyclohexane-1,4-dione,2,5-dicarboxylic acid alkylester.

From 2 to 200 mols, preferably from 7 to 100 mols and more preferably from 10 to 15 mols of water may be used per mol of cyclohexane-1,4-dione-2,5-dicarboxylic acid alkylester. The reaction with water is generally carried out at a temperature of from 80° to 250° C., preferably from 120° to 200° C. and in particular from 120° to 170° C., optionally under a pressure of from 1 to 200 bars.

The reaction may take from 1 to 24 hours, and preferably from 2 to 4 hours.

In a specific embodiment of the first stage of the process saponification is carried out in aqueous dimethylsulphoxide, and advantageously 0.05 to 2 parts by weight (based on the cyclohexane-1,4-dione-2,5-dicarboxylic acid alkylester) of an alkali halide (such as sodium or potassium chloride) are added to the reaction mixture in order to achieve shorter reaction times and/or lower temperatures.

The reaction mixture of the reaction with water can be further reacted immediately with malonic acid dinitrile, without further purification or without isolating an intermediate product, to produce 1,4-bis-(dicyanomethylene)-cyclohexane.

For this purpose, optionally after adding water or a suitable organic solvent as identified above, from 2 to 3 mols, preferably from 2.1 to 2.3 mols of malonic acid dinitrile and from 0 to 0.5 mols, preferably from 0 to 0.2 mols of a catalyst, (each based on 1 mol of cyclohexane-1,4-dione-dicarboxylic acid alkylester) can be added to the aqueous solution.

Organic or inorganic bases are suitable as catalysts, for example alkylamines such as diethylamine and triethylamine; arylamines such as aniline and N,N'-dimethylaniline; nitrogen-containing heterocycles such as pyridine and piperidine; aminocarboxylic acids such as aminoacetic acid and β-alanine; alkali carbonates such as sodium carbonate, potassium carbonate and sodium hydrogen carbonate; alkali hydroxides such as sodium hydroxide and potassium hydroxide; alkaline earth carbonates such as calcium carbonate; alkaline earth hydroxides such as calcium hydroxide and barium hydroxide; and ammonium salts such as ammonium acetate and ammonium propionate. The catalysts can be used on their own or as mixtures. A combination of from 0.0005 to 0.01 mols of β-alanine and from 0 to 0.2 mols of sodium hydrogen carbonate, based on the cyclohexane-1,4-dione-2,5-dicarboxylic acid alkylester which is used, is particularly preferred.

The reaction with malonic acid dinitrile generally takes from 5 to 15 minutes. The reaction temperature is preferably from 20° to 100° C.

The 1,4-bis-(dicyanomethylene)-cyclohexane can be recovered from the reaction mixture by filtration.

The yields obtained are 90 to 96% of the theoretical yield, based on the cyclohexane-1,4-dione-dicarboxylic acid alkylester which is used.

A specific variant of the present process comprises adding malonic acid dinitrile and optionally a catalyst or a catalyst mixture to the reaction mixture before saponification and decarboxylation, thus directly obtaining the 1,4-bis-(dicyanomethylene)-cyclohexane.

Production of 1,4-bis-(dicyanomethylene)-cyclohexane

EXAMPLE 1

114 parts by weight of cyclohexane-1,4-dione-2,5-dicarboxylic acid dimethylester and 200 parts by volume of water are heated at 170° C. for 4 hours in a stirrer-equipped autoclave. The cooled and depressurized solution is diluted with water to 1300 parts by volume, total volume. After adding 0.1 parts by weight of β-alanine, 20 parts by volume of saturated, aqueous sodium hydrogen carbonate solution and 72.6 parts by weight of malonic acid dinitrile, the mixture is stirred for 5 minutes at 50° C. It is then cooled, and the precipitated solids are filtered under suction and washed with water. 94.6 parts by weight (91% of the theoretical yield) of product are obtained having a melting range of from 204° to 208° C.

EXAMPLE 2

128 parts by weight of cyclohexane-1,4-dione-2,5-dicarboxylic acid diethylester are reacted as described in Example 1. 95.7 parts by weight (92% of the theoretical yield) of product are obtained having a melting range of from 206° to 209° C.

EXAMPLE 3

114 parts by weight of cyclohexane-1,4-dione-dicarboxylic acid dimethylester are reacted as described in Example 1, except that, after saponification, the mixture is not diluted with water. 93.6 parts by weight (90% of the theoretical yield) of product are obtained having a melting range of from 204° to 206° C.

EXAMPLE 4

57 parts by weight of cyclohexane-1,4-dione-2,5-dicarboxylic acid dimethylester, 120 parts by volume of dimethyl sulphoxide, 15 parts by volume of water and 5 parts by weight of sodium chloride are stirred for about 8 hours under reflux (about 130° C.) until evolution of $CO_2$ has ceased. The cooled solution is diluted with 500 parts by volume of water. 0.1 part by weight of β-alanine, 5.0 parts by weight of sodium hydrogen carbonate and 36.3 parts by weight of malonic acid dinitrile are added and the mixture is stirred for 10 minutes at 50° C. It is then cooled using an ice bath and the solids are filtered with suction, washed with water and dried. 48.3 parts by weight (93% of the theoretical yield) of product are obtained having a melting range of from 206° to 210° C.

$C_{12}H_8N_4$ (208) Calc.: 69.2% C, 3.8% H, 26.9% N; Found: 69.2% C, 3.8% H, 26.9% N.

We claim:

1. A process for the production of 1,4-bis-(dicyanomethylene)-cyclohexane, which comprises reacting cyclohexane-1,4-dione-2,5-dicarboxylic acid dialkyl ester, wherein each alkyl has 1–6 carbon atoms, with water under normal or elevated pressure of from 1 to 200 bars, and at a temperature of from 80° to 250° C., and reacting the resulting aqueous solution with malonic acid dinitrile at a temperature of from 0° to 100° C.

2. The process for the production of 1,4-bis-(dicyanomethylene)-cyclohexane according to claim 1, wherein said resulting aqueous solution is reacted with malonic acid dinitrile in the presence of a catlyst comprising a mixture of β-alanine and sodium hydrogen carbonate.

* * * * *